US00PP16405P2

(12) United States Plant Patent
Oliver

(10) Patent No.: US PP16,405 P2
(45) Date of Patent: Apr. 4, 2006

(54) ***HEUCHERA* PLANT NAMED 'PURPLE MOUNTAIN MAJESTY'**

(50) Latin Name: *Heuchera×hybrida*
Varietal Denomination: Purple Mountain Majesty

(76) Inventor: Charles Oliver, 921 Scottdale-Dawson Rd., Scottdale, PA (US) 15683

( * ) Notice: Subject to any disclaimer, the term of this patent is extended or adjusted under 35 U.S.C. 154(b) by 84 days.

(21) Appl. No.: 10/955,487

(22) Filed: Sep. 30, 2004

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent L. Bell
(74) *Attorney, Agent, or Firm*—C. A. Whealy

(57) ABSTRACT

A new and distinct cultivar of *Heuchera* plant named 'Purple Mountain Majesty', characterized by its full, densely foliated and uniformly mounded plant habit; purple and silver-colored foliage; numerous large white-colored flowers arranged on erect panicles; and excellent garden performance.

2 Drawing Sheets

Botanical classification/cultivar designation: *Heuchera× hybrida* cultivar Purple Mountain Majesty.

BACKGROUND OF THE INVENTION

The present invention relates to a new and distinct cultivar of *Heuchera* plant, botanically known as *Heuchera×hybrida* and hereinafter referred to by the name 'Purple Mountain Majesty'.

The new *Heuchera* is a product of a planned breeding program conducted by the Inventor in Scottdale, Pa. The objective of the breeding program is to create new *Heuchera* cultivars having good plant vigor, dense and uniform plant habit, and showy and attractive flower and leaf coloration.

The new *Heuchera* was discovered by the Inventor in a controlled environment in Scottdale, Pa., from seedling progeny from a cross-pollination made by the Inventor in May, 1999, of a proprietary selection of *Heuchera×hybrida* identified as code number H96-2C, not patented, as the female, or seed, parent with an unnamed selection of *Heuchera alba,* not patented, as the male, or pollen, parent. The new *Heuchera* was selected by the Inventor in May, 2000. The selection of this plant was based on its desirable flower and foliage coloration.

Asexual reproduction of the new *Heuchera* by cuttings in a controlled environment in Scottdale, Pa., since August, 2000, has shown that the unique features of this new *Heuchera* are stable and reproduced true to type in successive generations.

SUMMARY OF THE INVENTION

The cultivar Purple Mountain Majesty has not been observed under all possible environmental conditions. The phenotype may vary somewhat with variations in environment such as temperature and light intensity, without, however, any variance in genotype.

The following traits have been repeatedly observed and are determined to be the unique characteristics of 'Purple Mountain Majesty'. These characteristics in combination distinguish 'Purple Mountain Majesty' as a new and distinct cultivar of *Heuchera:*

1. Full, densely foliated and uniformly mounded plant habit.
2. Purple and silver-colored foliage.
3. Numerous large white-colored flowers arranged on erect panicles.
4. Excellent garden performance.

Plants of the new *Heuchera* can be compared to plants of the female parent, the proprietary *Heuchera* selection identified as H96-2C. In side-by-side comparisons conducted by the Inventor in Scottdale, Pa., plants of the new *Heuchera* differed from plants of the female parent selection in the following characteristics:

1. Plants of the new *Heuchera* were broader than plants of the female parent selection.
2. Plants of the new *Heuchera* had larger leaves than plants of the female parent selection.
3. Plants of the new *Heuchera* had taller inflorescences than plants of the female parent selection.
4. Plants of the new *Heuchera* and the female parent selection differed in flower shape and coloration.

Plants of the new *Heuchera* can be compared to plants of the male parent, the unnamed selection of *Heuchera alba.* In side-by-side comparisons conducted by the Inventor in Scottdale, Pa., plants of the new *Heuchera* differed from plants of the male parent selection in the following characteristics:

1. Plants of the new *Heuchera* had purple and silver-colored foliage whereas plants of the male parent selection had green-colored foliage.
2. Plants of the new *Heuchera* had smaller flowers than plants of the male parent selection.
3. Plants of the new *Heuchera* and the male parent selection differed in flower shape and coloration.

Plants of the new *Heuchera* can be compared to plants of the cultivar Harmonic Convergence, disclosed in U.S. Plant Pat. No. 11,111. In side-by-side comparisons conducted by the Inventor in Scottdale, Pa., plants of the new *Heuchera* differed from plants of the cultivar Harmonic Convergence in the following characteristics:

1. Plants of the new *Heuchera* had smaller leaves than plants of the cultivar Harmonic Convergence.

2. Plants of the new *Heuchera* had less silver-colored marbling on the upper surfaces of the leaves than plants of the cultivar Harmonic Convergence.
3. Plants of the new *Heuchera* had larger flowers than plants of the cultivar Harmonic Convergence.
4. Plants of the new *Heuchera* and the cultivar Harmonic Convergence differed in flower form and coloration.
5. Plants of the new *Heuchera* had shorter and narrower inflorescences than plants of the cultivar Harmonic Convergence.

Plants of the new *Heuchera* can also be compared to plants of the cultivar Silver Scrolls, disclosed in U.S. Plant Pat. No. 12,066. In side-by-side comparisons conducted by the Inventor in Scottdale, Pa., plants of the new *Heuchera* differed from plants of the cultivar Silver Scrolls in the following characteristics:

1. Plants of the new *Heuchera* had less silver-colored marbling on the upper surfaces of the leaves than plants of the cultivar Silver Scrolls.
2. Plants of the new *Heuchera* had larger flowers than plants of the cultivar Silver Scrolls.
3. Plants of the new *Heuchera* had shorter inflorescences than plants of the cultivar Silver Scrolls.

BRIEF DESCRIPTION OF THE PHOTOGRAPHS

The accompanying colored photographs illustrate the overall appearance of the new *Heuchera,* showing the colors as true as it is reasonably possible to obtain in colored reproductions of this type. Colors in the photographs may differ slightly from the color values cited in the detailed botanical description which accurately describe the colors of the new *Heuchera.*

The photograph on the first sheet comprises a side perspective view of a typical one-year old flowering plant of 'Purple Mountain Majesty'.

The photograph on the second sheet is a close-up view of a typical inflorescence of 'Purple Mountain Majesty'.

DETAILED BOTANICAL DESCRIPTION

In the following description, color references are made to The Royal Horticultural Society Colour Chart, 1995 Edition, except where generally terms of ordinary dictionary significance are used. The aforementioned photographs and following detailed botanical description describe plants grown in Scottdale, Pa. in a glass-covered greenhouse and under cultural conditions which approximate commercial practice. Plants were grown as single plants in one-gallon containers and were about one year old. During the production of the plants, day temperatures ranged from 15 to 26° C. and night temperatures ranged from 5 to 15° C.

Botanical classification: *Heuchera×hybrida* cultivar Purple Mountain Majesty.

Parentage:

*Female, or seed, parent.*—Proprietary selection of *Heuchera×hybrida* identified as code number H96-2C, not patented.

*Male, or pollen, parent.*—Unnamed selection of *Heuchera alba,* not patented.

Propagation:

*Type.*—By cuttings.

*Time to initiate roots.*—Summer: About 15 days at 23° C. Winter: About 21 days at 17° C.

*Time to produce a rooted cutting.*—Summer: About 45 days at 23° C. Winter: About 60 days at 17° C.

*Root description.*—Fine, fibrous and white in color.

*Rooting habit.*—Freely branching.

Plant description:

*Appearance.*—Perennial; basal rosette plant habit with leaves developing from the base; densely foliated; full, mounded and uniform plant habit with upright panicles with white-colored flowers. Vigorous growth habit.

*Plant size.*—Height, soil level to top of foliar plane: About 12 to 15 cm. Height, soil level to top of panicles: About 50 to 60 cm. Diameter or spread: About 30 to 40 cm.

*Foliage description.*—Arrangement: Basal rosette, simple. Length: About 6 to 9.5 cm. Width: About 6.5 to 9 cm. Shape: Rounded cordate; seven-lobed. Apex: Broadly obtuse, lobed. Base: Auriculate. Margin: Crenate with fine ciliation. Texture, upper and lower surfaces: Slightly rough; glabrous. Venation pattern: Palmate, reticulate. Color: Developing leaves, upper surface: 198A underlain with 187A. Developing leaves, lower surface: 187A. Fully expanded leaves, upper surface: 198A underlain with 187A; mottling, 196A. Fully expanded leaves, lower surface: 187A. Venation, upper surface: 198A underlain with 187A. Venation, lower surface: 187A. Petiole: Length: About 12 to 15 cm. Diameter: About 1.8 to 2 mm. Texture, upper and lower surfaces: Smooth. Color, upper and lower surfaces: 187B underlain with 198A.

Flower description:

*Appearance/arrangement.*—Single campanulate flowers arranged on numerous erect panicles; about 70 to 95 flowers and flower buds per flowering stem. Flowers face mostly outward to slightly downward. Flowering continuous. Flowers persistent. Flowers not fragrant.

*Time of flowering.*—Plants flower from May through July in Scottdale, Pa.; flowering continuous during this period.

*Inflorescence longevity.*—Individual inflorescences last about one week on the plant.

*Inflorescence size.*—Length: About 50 to 60 cm. Diameter: About 3.5 to 6.5 cm.

*Flower size.*—Diameter: About 6 mm. Depth (height): About 8 mm.

*Flower buds.*—Height: About 4 mm. Diameter: About 4.5 mm. Shape: Globular. Color, at stage of showing color: 59B.

*Sepals.*—Quantity/arrangement: Five sepals; radially symmetrical and fused at base. Calyx length: About 7 mm. Calyx diameter: About 6 mm. Shape: Elongate. Apex: Obtuse. Margin: Entire. Texture, upper and lower surfaces: Pubescent. Color, upper surface: Close to 155D. Color, lower surface: Close to 155D tinged with 59B.

*Petals.*—Quantity/arrangement: Five minute petals; radially symmetrical. Length: About 3.5 mm. Width: About 1.7 mm. Shape: Spatulate. Apex: Acute. Margin: Entire. Texture, upper surface: Smooth. Texture, lower surface: Slightly pubescent. Color, upper surface: Close to 155D. Color, lower surface: Close to 155D; pubescent, 59B.

*Flower bracts.*—Length: About 2.5 mm. Width: About 1 mm. Shape: Subulate. Apex: Acute. Margin: Serrate. Texture, upper and lower surfaces: Pubescent. Color, upper and lower surfaces: 59B.

*Peduncle.*—Strength: Strong. Aspect: Mostly upright. Length: About 30 to 36 cm. Diameter: About 2 mm. Texture: Smooth. Color: 59B.

*Pedicels.*—Strength: Strong. Aspect: About 60° from vertical. Length: About 3 mm. Diameter: About 0.2 mm. Texture: Pubescent. Color: 59B.

*Reproductive organs.*—Androecium: Stamen number: Five per flower. Anther shape: Oval. Anther length: About 0.4 mm. Anther width: About 0.3 mm. Anther color: 24A. Amount of pollen: Moderate. Pollen color: 24A. Gynoecium: Pistil number: Two per flower. Pistil length: About 7 mm. Stigma shape: Round. Stigma color: 157A. Style length: About 4 mm. Style color: 157A. Ovary color: 142C.

*Seed.*—Size: About 0.3 mm by 0.6 mm. Color: Close to 202A.

Disease/pest resistance: Resistance to pathogens and pests common to *Heuchera* has not been observed on plants grown under commercial conditions.

Weather/temperature tolerance: Plants of the new *Heuchera* have been observed to have excellent garden performance. Plants of the new *Heuchera* have demonstrated good tolerance to rain, wind, night temperatures as low as −35° C., and day temperatures as high as 45° C.

It is claimed:

1. A new and distinct cultivar of *Heuchera* plant named 'Purple Mountain Majesty', as illustrated and described.

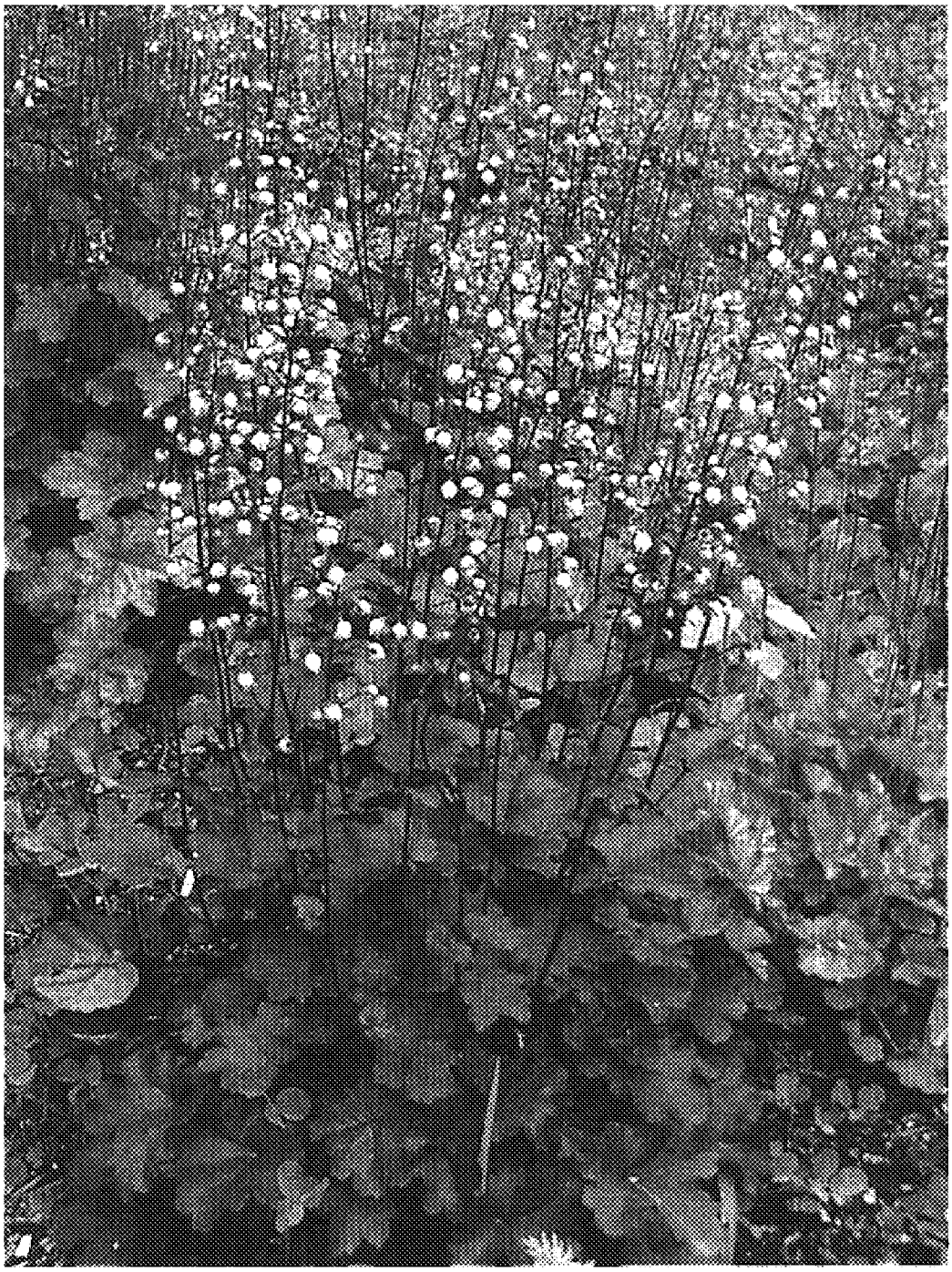

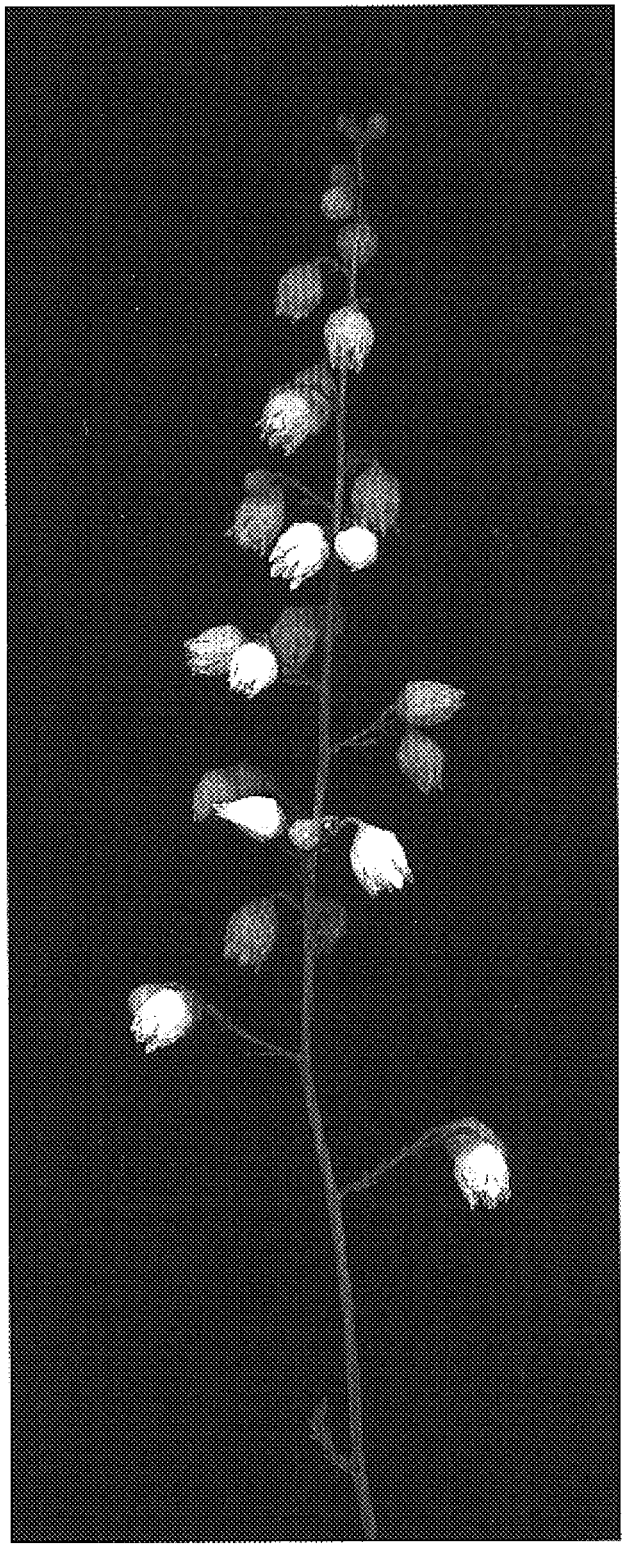

* * * * *